United States Patent
Bauer et al.

(10) Patent No.: US 6,452,042 B1
(45) Date of Patent: Sep. 17, 2002

(54) SUBSTITUTED PROPENOATES AND PROCESSES FOR THE PREPARATION THEREOF

(75) Inventors: Frank Bauer, Bonn (DE); Chitoor Subramaniam, East Brunswick, NJ (US)

(73) Assignee: Creanova, Inc., Piscataway, NJ (US)

( * ) Notice: Subject to any disclaimer, the term of this patent is extended or adjusted under 35 U.S.C. 154(b) by 0 days.

(21) Appl. No.: 09/494,256

(22) Filed: Jan. 28, 2000

(51) Int. Cl.$^7$ .............................................. C07C 67/30
(52) U.S. Cl. ...................... 560/212; 560/210; 560/130; 560/183; 560/186
(58) Field of Search ................................. 560/212, 210, 560/130, 183, 186

(56) References Cited

U.S. PATENT DOCUMENTS 4,808,595 A   2/1989  Hoffman, Jr. ............... 514/302

FOREIGN PATENT DOCUMENTS

JP   61289077   12/1986   ......... C07D/213/80

OTHER PUBLICATIONS

Sweet et al., J. Am. Chem. Soc., 95, 8741 (1973).*
Benoit, R., "Synthesis and Study of Chiral NADH Models in the Thieno[2,3–b]pyridine Series", *Journal Heterocyclic Chemistry*, 26, 1595 (1989).
Schenone, P., et al. "Reaction of 2–Dimethylaminomethylene–1,3–diones with Dinucleophiles. VII. Synthesis of Ehtyl and Methyl 2,4–Disubstituted 5–Pyrimidinecarboxylates", *Journal Heterocyclic Chem.*, 27, 295 (1990).
Holzer, "N–1 Substituted Ethyl 4–Pyrazolecarboxylates: Synthesis and Spectroscopic Investigations", *Journal Heterocyclic Chemistry* 30,865 (1993).
Kusumi et al., "Isolation, Structure and Synthesis of 4–Hydroxyisoxazole (Triumferol), A Seed Germination Inhibitor From an African Plant", *Tetrahedron Letters, vol. 22, No. 36*, pp. 3451–3454, (1981).
Genin, Michael, et al., "Nitrogen–Carbon Linked (Azolphenyl) oxazolidinones with Potent Antibacterial Activity Against the Fastidious Gram–Negative Organisms Haemophilus Influenzae and Moraxella Catarrhalis", *J. Med. Chemistry*, 41, 5144–5147, (1998).
Bertz et al., "New Preparations of Ethyl 3,3–Diethoxypropionate and (Ethoxycarbonyl)malonidialehyde. Cu(I)–Catalyzed Acetal Formation from Conjugated Triple Bond", *J. Org. Chem.* 47, 2216–2217, (1982).
Von V. Prelog, "Zur Kenntnis Der Phenol–Synthese Aus β–Dicarbonyl–Verbindungen und Ketonen" *Helvetica Chimica Acts, vol. XXXIV, Fasciculus I No. 27*, (1951).
Reichardt, "Vilsmeier–Formylierung von Acetonitril", *Synethesis*, p. 538, (1970).
Bertz et al., "Synthesis of Biocyclo[3.3.1]Nonane Derivatives Under Physiological Conditions", *Angew.Chem. Int. Ed. Engl.* 21 No. 4 pp. 306–307 (1982).

* cited by examiner

*Primary Examiner*—Sreeni Padmanabhan
*Assistant Examiner*—Robert W. Deemie
(74) *Attorney, Agent, or Firm*—Abelman, Frayne & Schwab

(57) ABSTRACT

Substituted propenoates are prepared by eliminating an alcohol from a substituted malondialdehyde acetal, optionally in the presence of a homogeneous or heterogeneous catalyst.

66 Claims, No Drawings

SUBSTITUTED PROPENOATES AND PROCESSES FOR THE PREPARATION THEREOF

FIELD OF THE INVENTION

The present invention relates to substituted propenoates and processes for the preparation thereof.

DESCRIPTION OF THE BACKGROUND

Substituted propenoates of the general formula (I):

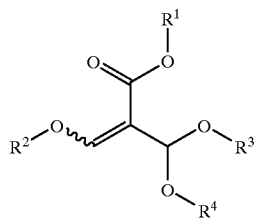

in which $R^1$, $R^2$, $R^3$, and $R^4$ are the same or different alkyl groups, cycloalkyl groups, aralkyl groups, or aryl groups with up to 12 carbon atoms constitute valuable building blocks in the synthesis of, for example, heterocycles such as pyrazoles, pyrimidines, and isoxazoles.

As demonstrated in a co-pending, commonly assigned patent application, filed on even date herewith, entitled "Process for Preparing Substituted Acetals of Malondialdehyde", the disclosure of which is incorporated herein by reference, the use of malondialdehyde acetals of general formula (II)

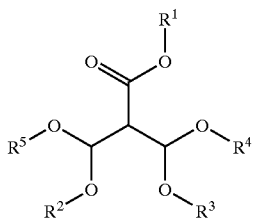

in which $R^1$, $R^2$, $R^3$, $R^4$ and $R^5$ are the same or different alkyl groups, cycloalkyl groups, aralkyl groups or aryl groups with up to 12 carbon atoms for the preparation of heterocycles is advantageous over the use of the free aldehydes of general formula (III):

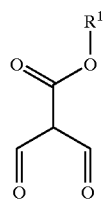

in which $R^1$ is an alkyl group, cycloalkyl group, aralkyl group or aryl group, with up to 12 carbon atoms.

However, it has been found that the compounds of general formula II normally are less reactive than the free aldehydes of general formula III. In fact, upon use of the compounds of general formula II for the preparation of heterocycles, it was found that the addition of water to the reaction mixture can be advantageous. Most likely, this water-addition leads to hydrolysis or partial hydrolysis of the diacetals to the free aldehydes, which then react to form the heterocycles. The addition of water to the reaction mixtures in order to activate the compounds of general formula II is often undesirable, for example, with respect to a potential hydrolysis of the ester-group $COOR^1$. Thus, a need exists for easily accessible, thermally stable compounds that can be used as substitutes for the compounds of general formula II, provided, however, that these compounds are more reactive, for example, in the synthesis of heterocycles, as well as a process for the preparation of these compounds.

SUMMARY OF THE INVENTION

It is an object of the present invention to provide substituted propenoates of general formula I

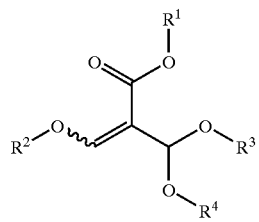

in which $R^1$, $R^2$, $R^3$ and $R^4$ are the same or different alkyl groups, cycloalkyl groups, aralkyl groups, or aryl groups with up to 12 carbon atoms as a new class of building blocks, as well as, processes for the preparation thereof.

DETAILED DESCRIPTION OF THE PREFERRED EMBODIMENTS

Substituted propenoates of the general formula (I):

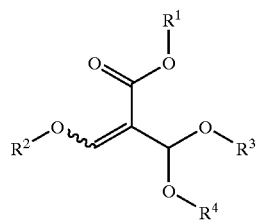

in which $R^1$, $R^2$, $R^3$ and $R^4$ are the same or different alkyl groups, cycloalkyl groups, aralkyl groups, or aryl groups with up to 12 carbon atoms constitute valuable building blocks in the synthesis of, for example, heterocycles, such as pyrazoles, pyrimidines, and isoxazoles. They can be used advantageously as substitutes for the compounds of general formula II and III. While the compounds of general formula II are easily accessible from orthoesters and substituted acrylates, as disclosed in a co-pending application of even date entitled "Process for Preparing Substituted Acetals of Malondialdehyde", they were generally found to be less reactive than the compounds of general formula III. As will be shown later, the compounds of general formula I combine the advantages of easy accessibility, low formation of salt waste, and high thermal stability with the added advantage of a higher reactivity as compared to the compounds of general formula II. The increased reactivity results from the presence of the enol-ether structural element in the compounds of general formula I. The preparation of heterocycles from the compounds of general formula I, instead of the compounds of general formula II, has the additional advantage of leading to the formation of smaller amounts of alcohols, i.e., no $R^5$-OH is formed.

2-ethoxycarbonyl-malondialdehyde in particular has found a broad range of applications, for example, in the synthesis of pyridine derivatives (JP 61,289,077), pyrimidines (Schenone, P., Sansebastiano, L., Mosti, L., *J. Heterocycl. Chem.* 1990, 27 (2), 295), pyrazoles (Holzer, W., Seiringer, G., *J. Heterocycl. Chem.* 1993, 30, 865), isoxazoles (Kusumi, T. et al., *Tetrahedron Letters* 22 (1981), 36, 3451), phenolic compounds (Prelog, V., Wuersch, J., Koenigsbacher, K., *Helv. Chim. Acta* 1951, 34, 258; Bertz, S. H., Dabbagh, G., *Angew. Chem. Int. Ed. Engl.* 1982, 21, 306) and pharmaceuticals (U.S. Pat. No. 4,808,595; Genin, M., *J. et al. J. Med. Chem.* 1998, 41, 5144), which is, at least, partially due to the availability of this compound by the condensation of ethyl-3,3-diethoxypropionate with ethyl formate in the presence of base (Bertz, S. H., Dabbagh, G., Cotte, P., *J. Org. Chem.* 1982, 47, 2216). However, besides providing the free aldehyde instead of a diacetal, this approach suffers from several major drawbacks such as expensive (ethyl-3,3-diethoxypropionate) or difficult to handle (NaH) starting materials and the formation of wastewater.

Especially, in the use of the compounds of general formula I for the preparation of heterocycles, the alcohols of general formula $R^1$OH and/or $R^2$OH and/or $R^3$OH and/or $R^4$OH are liberated. In order to achieve high space-time-yields and to facilitate the isolation procedures for the compounds of general formula I, it is generally desirable to limit the molecular weight of the compounds of general formula I. Consequently, those compounds where $R^1$, $R^2$, $R^3$, and $R^4$=methyl and ethyl are especially preferred.

It has been found that the compounds of general formula I can advantageously be reacted with reactants, such as hydroxylamines, hydroxylamine salts, hydrazine, hydrazine salts, formamide, amidines, amidine salts, guanidines, guanidine salts, aminoguanidines, aminoguanidine salts, alkyl-3-aminoacrylates, cycloalkyl-3-aminoacrylates, aryl-3-aminoacrylates, aralkyl-3-aminoacrylates, nitroguanidine, nitroguanidine salts, O-alkyl-isoureas and their salts, O-cycloalkyl-isoureas and their salts, O-aralkyl-isoureas and their salts, O-aryl-isoureas and their salts, S-alkyl-isothioureas, S-cycloalkyl-isothioureas, S-aralkyl-isothioureas, S-aryl-isothioureas respective S-alkyl-isothiouronium salts, S-cycloalkyl-isothiouronium salts, S-aralkyl-isothiouronium salts, S-aryl-isothiouronium salts, thiourea, and urea to form a heterocycle.

The compounds of general formula I were previously unknown. Their production on a commercial scale requires a process or processes that gives high yields based on easily accessible starting materials without the formation of excessive amounts of salt waste. It has been found that this is achieved in a simple manner by the elimination of an alcohol of general formula $R^5$OH from the compounds of general formula II. Several commercially viable processes were identified that allow for the elimination of an alcohol $R^5$OH from the compounds of general formula II. The simplest process comprises heating the compounds of general formula II in the presence of an appropriate catalyst, while removing the formed alcohol by distillation, such as vacuum distillation or azeotropic distillation.

Acidic catalysts, preferably mild Lewis acids, especially preferred mildly Lewis acidic heterogeneous catalysts are used. Examples of such catalysts are salts, such as $NH_4Cl$, $(NH_4)_2SO_4$, $NR_3HCl$, $NR_3HCl$, transition metal salts, such as $Zn(acac)_2$, $ZnSO_4$, $Fe(OAc)_2$, $ZnCl_2$, $Zn(OAc)_2$, acetic acid, aluminum oxide, zinc oxide, zeolites, montmorillonites, or metal-exchanged zeolites and montmorillonites.

The amount of catalyst required to give reasonable reaction rates was found to cover a broad range and depended to a great extent on the nature of the catalyst. Normally, catalyst-concentrations below 0.000001 w/w-%, with reference to the compounds of general formula II, led to unacceptably long reaction-times, even with the use of highly reactive Lewis acids. On the other hand, especially if the process according to the invention is conducted continuously using a heterogeneous catalyst and provided the reaction mixture is sufficiently diluted, it has been found advantageous to use catalyst concentrations as high as 5000 w/w-%, with reference to the compounds of general formula II. It is a special advantage of the process according to the invention, that normally very small amounts of catalyst, for example 0.1 mole-% with reference to the compounds of general formula II, are sufficient to give commercially acceptable reaction rates. In accordance with principally known procedures (JP 52097905, JP 57026572), the removal of the alcohols of general formula $R^5$OH is not limited to distillation. By the use of trapping agents, such as acid anhydrides, particularly mild reaction conditions can be realized.

The temperatures that are required in order to achieve reasonable reaction rates strongly vary with the type of catalyst used. While the reaction has been found to proceed in the broad range from about 20° C. to about 300° C., good yields of the compounds of general formula I are achieved in the range of about 50° C. to about 200° C., preferably from about 130° C. to about 190° C.

The major disadvantage of this process is the formation of high-boiling byproducts. This byproduct-formation can result in substantial product losses, especially when using relatively strong Lewis acids or protic acids. Also, there is the principal risk of a potentially hazardous polymerization of the compounds of general formula I under the reaction conditions. If the reaction is run continuously, a complete conversion of the starting materials of general formula II, i.e. >99.5% %, can be difficult to achieve.

As expected, the formation of high-boiling byproducts can be reduced by the addition of an appropriate inert solvent. However, this approach leads to a decrease in the space-time-yield. A better alternative is to feed the compounds of general formula II to a catalyst-containing high-boiling inert solvent, such as a high molecular weight polyethyleneglycole ether at elevated temperatures of about 60° C. to about 300° C. and to remove the compounds of general formula I from the reaction zone via distillation, preferably in vacuo. Technically, this thermolysis can be carried out advantageously using a wiped-film evaporator, a short-path evaporator, or a thin-film evaporator.

It has been found that the compounds of general formula I can be prepared without any significant formation of high-boiling byproducts by the gas phase thermolysis of the compounds of general formula II in the presence of a, preferably heterogeneous, catalyst. Examples of suitable catalysts are, preferentially acidic, zeolites, metal-doped zeolites, montmorillonites, metal-exchanged montmorillonites, such as K 5-Fe, silicas or metal oxides, such as aluminium oxide or zinc oxide. Strongly acidic heterogenous catalysts, especially if relatively high temperatures are applied, are found to catalyze the fragmentation of the compounds of general formula II, besides the desired formation of the compounds of general formula I. Thermolysis in the absence of a catalyst was found to be very ineffective, as, for example, demonstrated by methyl-3,3-dimethoxy-2-dimethoxymethyl propionate being thermally stable up to at least 160° C. In order to exclude condensation of the products of general formula I and of the starting materials of general formula II, application of vacuum and/or the addition of an inert gas such as nitrogen, or argon, or an inert organic solvent, was found advantageous. The required temperatures vary a great deal with the type of catalyst used, as well as, with the. type of starting material of general formula II. While the lower temperature limit is solely dictated by the requirement that the starting materials of general formula II, as well as the products of general formula I, have to remain gaseous, temperatures as high as 400° C. can be applied in order to achieve complete conversion of the compounds of general formula II. Acceptable reaction rates are usually achieved in the temperature range from about 80° C. to about 280° C. However, to a chemist of ordinary skill in the art, this process variant according to the invention can easily be optimized with respect to a full conversion of the individual starting materials, as well as, commercially acceptable reaction rates and high yields, for example, 90% of the theoretical yield based on the compounds of general formula II.

Surprisingly, it is normally not necessary to prepare the compounds of general formula I from the isolated compounds of general formula II. In a preferred embodiment of the process according to the present invention, the compounds of general formula I are directly prepared from the substituted acrylates of general formula IV

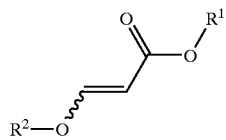

IV in which $R^1$ and $R^2$ are as defined above, and orthoformates of general formula V

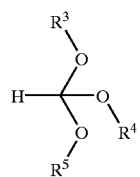

V in which $R^3$, $R^4$, and $R^5$ are as defined above. In the direct preparation of the compounds of general formula I from the compounds of general formula IV and V, it is principally possible to use the same catalysts as for the known preparation of the compounds of general formula II as disclosed in a co-pending application of even date entitled "Process for the Preparation of Substituted Acetals of Malondialdehyde. Examples of such catalysts are $SnCl_4$, $SnCl_3Ph$, $AlCl_3$, $BBr_3$, $SbF_5$, $ZnCl_2$, $FeCl_3$, $BF_3$, $TiCl_4$, homogeneous catalysts on an inert support, such as $FeCl_3$ on $SiO_2$, Envirocats®, or heterogeneous catalysts such as acidic montrnorillonites, zeolites, metal-exchanged montmorillonites, metal-exchanged zeolites, etc. However, since even in the presence of such strong Lewis acids, elevated temperatures were required to convert the primarily formed compounds of general formula II to the desired compounds of general formula I, it was found advantageous to use different, normally milder, catalysts for the elimination step. In fact, the catalysts that favor the addition of compounds of general formula V to the compounds of general formula IV were found to catalyze the polymerization of the compounds of general formula I even at temperatures as low as 30° C. in the case of $BF_3$-etherate. Consequently, it is advantageous to neutralize strongly acidic Lewis acid catalysts before the desired elimination of the alcohols $R^5OH$ takes place. In a preferred embodiment of the process according to the invention, however, heterogeneous catalysts are being used for at least one of the reaction steps, so that a neutralization of the reaction mixture is either not required at all, or the formation of salt-waste and the costs associated with its removal and disposal are minimized. Obviously, in the case of the use of a heterogeneous catalyst for the addition step, either a homogenous or a heterogeneous catalyst has to be added in order to facilitate the elimnnation step.

In any case and similar to the preparation of the compounds of general formula II from the compounds of general formula IV and V, it has been found to be advantageous to use up to a 10-fold molar excess, preferably a 1.2-fold to 3-fold excess, of the compounds of general formula V over the compounds of general formula IV.

Surprisingly, when relatively strong homogeneous Lewis acids, such as $SnCl_4$ or cheap $FeCl_3$ are used as catalysts for the reaction of the compounds of general formula IV and V, upon subsequent neutralization of the catalysts with a base, such as sodium methylate solution or $Na_2CO_3$, and mechanical removal of the salt waste, no further addition of catalyst was required for the in situ conversion of the compounds of general formula II into the compounds of general formula I. While it is not even necessary to remove the salts resulting from the neutralization of the Lewis acid, better yields are usually achieved if at least the majority of the salts are mechanically removed prior to the conversion of the compounds of general formula II to the compounds of general formula I. On the other hand, a practically quantitative precipitation of the salts can be induced, for example, by the addition of unpolar solvents like cyclohexane. Normally this is not desirable since the presence of some of the salt-waste has been found to catalyze the elimination of $R^5OH$ from the compounds of general formula I. It has been found that, in order for the (remaining) salt-waste to be catalytically active with respect to the conversion of primarily formed compounds of general formula II to the compounds of general formula I, it is crucial to conduct the neutralization to a defined degree. Strong over-neutralization is to be avoided. The ideal amount of base to be added in order to achieve the compounds of general formula I in high yields of, for example >90%, based on the converted starting materials of general formula IV, and high purities of, for example >99%, has to be determined individually for each combination of the compounds of general formula IV, V, and the catalyst used.

Depending on the type of catalyst used for the primary reaction of the compounds of general formula IV and V, as well as the type and amount of base added, it can still be advantageous to additionally add a catalyst, preferably a mildly acidic or neutral catalyst, such as $ZnOAc$, $ZnSO_4$, $Fe(OAc)_2$, $Zn(acac)_2$, $Mn(OAc)_2$, $ZnO$, etc., which facilitates the elimination of the alcohols of general formula $R^5OH$ from the compounds of general formula II. As mentioned earlier, in a preferred embodiment of this process variant according to the present invention, this additionally used catalyst is heterogeneous in nature. Under the above conditions, the elimination normally requires higher temperatures than those required for the reaction of the compounds of general formula IV and V, i. e. from about 40° C. to 280° C., preferably from about 80° C. to about 230° C., with from about 130° C. to about 190° C. being especially preferred. The elimination of the alcohols of general formula $R^5OH$ can, for example, be induced by heating the reaction mixtures to the desired temperature until complete conversion is achieved, by feeding the reaction mixture into a high boiling inert solvent, or by conducting the thermolysis on a WIFE. In any case, it was found advantageous to remove the alcohols of general formula $R^5OH$, as well as, the products of general formula I from the reaction zone as quickly as possible. Consequently, in a preferred embodiment of the process according to the present invention, at least the elimination step is carried out continuously. Especially in the cases where the compounds of general formula I are particularly sensitive towards the reaction conditions, the WIFE-thermolysis is preferred. The application of vacuum during the elimination step was found to be generally advantageous since it facilitates the removal of the alcohols of general formula $R^5OH$, as well the distillation of the compounds of general formula I, whereby they are removed from the reaction-zone.

Surprisingly, under these conditions of the process according to the present invention, practically no formation of high-boiling byproducts is observed. High yields of, for example, 90% of theory based on converted starting material of general formula IV can be achieved. In fact, within experimental error, the molar yields of the compounds of general formula I, based on converted starting materials of general formula IV, are normally the same as the yields for the compounds of general formula II according to co-pending patent application of even date entitled "Process for Preparing Substituted Acetals of Malondialdehyde".

Due to the lower boiling points of the non-converted starting materials of general formulas IV and V, respectively, the alcohols of general formula $R^5OH$ as compared to the products of general formula I, the isolation of the products of general formula I can easily be achieved by fractional distillation. In the case of the direct synthesis of the compounds of general formula I from the starting materials of general formula IV and V, non-converted starting materials of general formula IV and V can be reused after their recovery. It is, in fact, a special advantage of this process variant according to the invention, that, by appropriate choice of conditions, the compounds of general formula IV are recovered in a relatively pure form and that, in particular, any contamination with the compounds of general formula VI

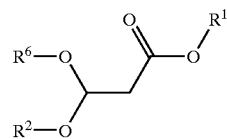

in which $R^6=R^1$, $R^2$, $R^3$, $R^4$ or $R^5$, which cannot directly react with the compounds of general formula V, is negligible. Apparently, this is due to the salt-wastes of the respective catalysts that catalyze the elimination of the alcohols $R^5OH$ from the compounds of general formula II also catalyzing the elimination of the alcohols of general formula $R^6OH$ from the compounds of general formula VI. However, it has been found that, depending on the acidity of the salt-wastes of the respective catalysts, as well as the temperatures at which any unconverted compounds of general formula V are exposed to the salt-wastes of the respective catalysts, the unconverted compounds of general formula V can partially decompose to form low-boiling byproducts during their recovery.

Consequently, in an especially preferred process variant according to the present invention, exposure of the compounds of general formula V to salt wastes of the respective catalysts that cause partial decomposition of the compounds of general formula V is avoided, while at the same time, the presence of salt-wastes of the respective catalysts which favor the elimination of the alcohols of general formula $R^6OH$ from the compounds of general formula VI, is assured. This can, for example, be achieved by using a heterogeneous catalyst for the primary reaction of the compounds of general formula IV and V, subsequent recovery of any unconverted starting materials of general formula V, preferably by distillation, and especially preferred by fractional distillation, and exposure of the remaining reaction mixture to a catalyst, preferably a heterogeneous catalyst, in order to achieve complete conversion to the compounds of general formula I, whereby any unconverted starting material of general formula IV is recovered without any contamination with the compounds of general formula VI.

If a homogenous catalyst is used to catalyze the initial reaction of the compounds of general formula IV and V, the reaction mixture can be over-neutralized with bases like sodium alcoholates, sodium carbonate, potassium carbonate, etc. whereupon any unconverted compounds of general formula V can be recovered, preferably by distillation, especially preferred by fractional distillation, without any losses due to acid-catalyzed decomposition. The remaining reaction mixture can then be exposed to a catalyst, preferably a heterogenous catalyst, in order to achieve complete conversion to the compounds of general formula I, and in order to allow for the isolation of any unconverted starting material of general formula IV without any contamination with the compounds of general formula VI.

It is not necessary to conduct the elimination of the alcohols of general formula $R^5OH$ from the compounds of general formula II by two consecutive process steps. In a preferred embodiment of the process according to the present invention, the alcohols of general formula $R^5OH$ are eliminated from the compounds of general formula II during the distillation. Due to the great difference in boiling points, separation of the compounds of general formula I from the liberated alcohols of general formula $R^5OH$ can be achieved by, for example, fractional condensation and/or subsequent fractional distillation.

For the further purification of the compounds of general formula I standard procedures, such as crystallization, column chromatography, etc. can be used. In a preferred embodiment of the process according to the present invention, the products of general formula I are further purified by distillation, especially preferred is the use of a wiped-film evaporator, a short-path evaporator, or a falling-film evaporator. It is a special advantage of the process according to the present invention, however, that as long as complete conversion of the compounds of general formula II is assured, no significant amounts of byproducts with a boiling point similar to that of the products of general formula I are formed. Therefore, the compounds of general formula I can be obtained in high purities, for example 98%, by short-path distillation of the crude.

While an alternative work-up of the reaction mixture, which comprises bringing it into contact with water, preferably an aqueous solution of a base like sodium hydroxide, and subsequent removal of the aqueous phase, was found to be viable, this approach suffers from the disadvantage of leading to the formation of contaminated wastewater.

Having described the present invention, reference will now be made to certain examples, which are provided solely for purposes of illustration and are not intended to be limitative.

EXAMPLE 1

Methyl-3-methoxy-2-dimethoxymethyl Propenoate

In a 250 ml 3-neck round-bottomed glass flask equipped with a magnetic stirring bar, thermometer, 15 cm Cerapack distillation column, and distillation head, were placed 30.00 g methyl-3,3-dimethoxy-2-dimethoxymethyl propionate. 200 mg $(NH_4)_2SO_4$ were added with stirring. Over a period of 4 hours, the mixture was slowly heated to 190° C. while removing low-boilers by the application of vacuum (200 mbar). By improving the vacuum, 21.45 g of a slightly yellow liquid was received. A GC-analysis of the liquid revealed an assay of 60.2 FID-area-% besides 32.0 FID-area-% of unconverted starting material which refers to a yield of approximately 65.0% of theory based on converted methyl-3,3-dimethoxy-2-dimethoxymethyl propionate).

EXAMPLE 2

Methyl-3-methoxy-2-dimethoxymethyl Propenoate

The procedure given in example 1 was followed except that 0.50 g of $Zn(acac)_2$ was used as the catalyst. Distillation upon complete conversion of the methyl-3,3-dimethoxy-2-dimethoxymethyl propionate gave 23.37 g of colorless methyl-3-methoxy-2-dimethoxymethyl propenoate (89.3% of the theoretical yield). GC-analysis of the product revealed an assay of 98.1 FID-are-%.

EXAMPLE 3

Methyl-3-methoxy-2-dimethoxymethyl Propenoate
(or comparison)

The procedure given in example 1 was followed except that 100 mg of $BF_3 * OEt_2$ was used as the catalyst. Distillation upon complete conversion of the methyl-3,3-dimethoxy-2-dimethoxymethyl propionate gave only 2.8 g of methyl-3-methoxy-2-dimethoxymethyl propenoate. The distillation residue was determined to 22.1 g.

EXAMPLE 4

Methyl-3-methoxy-2-dimethoxymethyl Propenoate

A 250-ml 3-neck round-bottomed flask, equipped with a vacuum-mantled distillation adapter, and a dropping funnel, was charged with 10.00 g of polyethylene glycole dimethylether (MW=1000). The polyethyleneglycole ether was heated to 225° C. under a vacuum of approximately 4 mbar. Within 60 minutes, 20.00 g of methyl-3,3-dimethoxy-2-dimethoxymethyl propionate were fed to the polyethylene glycole ether. The resulting vapors were passed over a fixed (16"×2.25") bed comprising of zinc oxide beads (3 nun) that was heated to 240° C. Two fractions were condensed at 18° C. respective -10° C. GC-analysis of the first fraction (15.71 g) revealed a methyl-3-methoxy-2-dimethoxymethyl propenoate assay of 96.2%; GC-analysis of the second fraction (3.21 g), which basically consisted of methanol, revealed a methyl-3-methoxy-2-dimethoxymethyl propenoate assay of 15.23%. Both fractions did not contain any unconverted starting material, so that the methyl-3-methoxy-2-dimethoxymethyl propenoate yield can be calculated to 91% of theory.

EXAMPLE 5

Methyl-3-methoxy-2-dimethoxymethyl Propenoate
(or comparison)

The procedure given in example 4 was followed, except that montmorillonite K-306® beads (Suidchemie GmbH) were used as the heterogeneous catalyst. Two condensate fractions were received, the first one of which (12.52 g) comprised of 36.1 FID-area-% methyl-trans-3-methoxyacrylate, 28.6 FID-area- % methyl-3,3-dimethoxy-2-dimethoxymethyl propionate and 31.4 FID-area- % methyl-3-methoxy-2-dimethoxymethyl propenoate.

EXAMPLE 6

Methyl-3-methoxy-2-dimethoxymethyl Propenoate

A 5-1 3-neck round-bottomed glass flask, equipped with a mechanical stirrer, nitrogen inlet, reflux condenser, and thermometer, was charged with 1908.0 g of trimethyl orthoformate. With stirring, 72.9 g of anhydrous irontrichloride were fed over a period of 30 minutes with stirring, whereby, the access of air was excluded through purging with nitrogen. During the catalyst addition, the temperature was maintained below 18° C. To the resulting clear solution, 522.0 g of methyl-trans-3-methoxyacrylate were added and the mixture was stirred at 20° C. to 22° C. for 26 hours. The catalyst was neutralized by the addition of 233.86 g 30 w/w-% of a sodium methylate solution in methanol, whereby, the temperature was kept between 10° C. and 20° C. through external cooling (pH of a sample after the addition of demineralized water: "7"). To the resulting slurry, 87.0 g Celite R 521® were added and the mixture was filtered (sparkler filter, 50 psi). After washing the filter-cake with 150.00 g methyl formate, the clear yellow filtrate was fractionally distilled (25-cm packed column), whereby the pot-temperature during the distillation of the methyl-3-methoxy-2-dimethoxymethyl propenoate was maintained at 165° C. to give 405.78 g of methyl-3-methoxy-2-dimethoxymethyl propenoate besides 1162.49 g of recovered trimethyl orthoformate and 211.13 g of recovered methyl-trans-3-methoxyacrylate. GC-analysis of the methyl-3-methoxy-2-dimethoxymethyl propenoate revealed an assay of 99 FID-area-%. The distillation residue was determined to 10.10 g.

EXAMPLE 7

Methyl-3,3-dimethoxy-2-dimethoxymethyl Propionate

The procedure given in example 6 was followed except that the reaction mixture was slightly over-neutralized (pH of a sample after the addition of de-mineralized water: "9") and that the pot-temperature during the distillation was limited to 120° C. By this means, 473.26 g of methyl-3,3-dimethoxy-2-dimethoxymethyl propionate, with an assay of 99 FID-area-%, were isolated.

EXAMPLE 8

Methyl-3-methoxy-2-dimethoxymethyl Propenoate

The procedure given in example 6 was followed except that the catalyst-addition was carried out at a temperature of 0° C. and that the initial reaction of methyl-trans-3-methoxyacrylate with trimethyl orthoformate was carried out at a temperature of 5° C. Besides, approximately one third of the $FeCl_3$-catalyst was fed to the reaction mixture over the period of the reaction, the initial reaction mixture was over-neutralized (pH of a sample after the addition of de-mineralized water: "9") and, after the isolation of unconverted trimethyl orthoformate, 12.0 g zinc acetate were added. By this means, 549.47 g of methyl-3-methoxy-2-dimethoxymethyl propenoate could be isolated. 1415.77 g trimethyl orthoformate and 215.58 g methyl-trans-3-methoxyacrylate were recovered. This refers to an isolated methyl-3-methoxy-2-dimethoxymethyl propenoate yield of 93.7% of theory based on converted methyl-trans-3-methoxyacrylate and 53.3% of theory based on converted trimethyl orthoformate.

What is claimed is:

1. Substituted propenoates of general formula I:

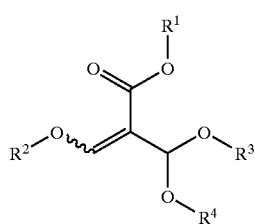

in which $R^1$, $R^2$, $R^3$, and $R^4$ are the same or different alkyl groups, cycloalkyl groups, aralkyl groups, or aryl groups with up to 12 carbon atoms.

2. A process for the preparation of the compounds of general formula I,

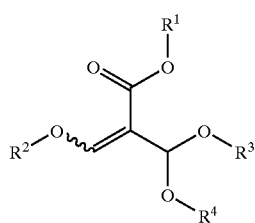

which comprises eliminating an alcohol of general formula $R^2OH$, $R^3OH$, $R^4OH$, or $R^5OH$ from a malondialdehyde acetal of general formula (II):

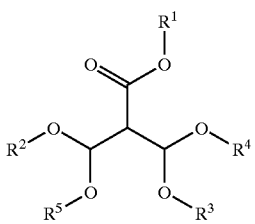

in which $R^1$, $R^2$, $R^3$, $R^4$, and $R^5$ are the same or different alkyl groups, cycloalkyl groups, aralkyl groups, or aryl groups with up to 12 carbon atoms.

3. The process of claim 2, wherein the elimination is carried out in the presence of a catalyst.

4. The process of claim 3, wherein the catalyst is acidic.

5. The process of claim 4, wherein the catalyst is a mild Lewis acid.

6. The process of claim 3, wherein the catalyst is a salt.

7. The process of claim 6, wherein the catalyst is a transition metal salt.

8. The process of claim 7, wherein the catalyst is a zinc salt or an iron salt.

9. The process of claim 8, wherein the salt is selected from the group consisting of Zn(ac ac)$_2$, ZnSO$_4$, ZnCl$_2$, Zn(OAc)$_2$ and Fe(OAC)$_2$.

10. The process of claim 3, wherein the elimination is carried out in the presence of a heterogenous catalyst.

11. The process of claim 10, wherein the heterogeneous catalyst is selected from the group of oxides, zeolites, silicas, montmorillonites, or metal-exchanged zeolites and montmorillonites.

12. The process of claim 11, wherein the oxides are metal oxides selected from the group consisting of aluminum oxide and zinc oxide.

13. The process of claim 3 or 10, wherein the catalyst concentration is between 0.000001% and 5000%, by weight, with reference to the compounds of general formula II.

14. The process of claim 2, 3, 4, 5, 6, 7, 8, 9, 10, 11, or 12, wherein the elimination is carried out in the temperature range from about 20° C. to about 300° C.

15. The process of claim 14, wherein the elimination is carried out between about 50° C. and about 200° C.

16. The process of claim 15, wherein the elimination is carried out between about 130° C. and about 190° C.

17. The process of claims 2, 3, 4, 5, 6, 7, 8, 9, 10, 11 or 12 wherein the elimination is carried out in the presence of an inert solvent.

18. The process of claims 2, 3, 4, 5, 6, 7, 8, 9, 10, 11, 12, 15, or 16, wherein the compounds of general formula II are fed to a catalyst-containing high-boiling inert solvent and the products of general formula I are removed by distillation.

19. The process of claim 18, wherein the removal of the products of general formula I by distillation is conducted in vacuo.

20. The process of claim 19, wherein the reaction is carried out on a falling-film evaporator, a wiped-film evaporator, or a short-path evaporator.

21. The process of claim 20, wherein the process is a continuous process.

22. The process of claims 2, 3, 4, 5, 6, 7, 8, 9, 10, 11, or 12 wherein the elimination is carried out in the gas phase.

23. The process of claim 22, wherein the elimination in the gas phase is carried out in vacuo.

24. The process of claim 23, wherein the elimination reaction is carried out in the presence of an inert gas or an inert organic solvent.

25. The process of claim 22, wherein the elimination is carried out within the temperature range of from about 50° C. to 400° C.

26. The process of claim 22, wherein the temperature range is from about 80° C. to about 280° C.

27. The process of claim 2, wherein the compound of general formula I is prepared by the reaction of the compound of general formula IV

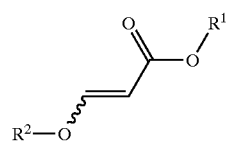

in which $R^1$ and $R^2$ are as defined above, and an orthoformate of general formula V

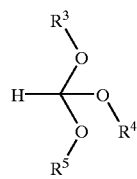

in which R³, R⁴, and R⁵ are as defined above.

28. The process of claim 27, wherein an up to 10-fold molar excess of the orthoformate of general formula V is used with reference to the compounds of general formula IV.

29. The process of claim 28, wherein about a 1.2-fold to 3-fold excess of the orthoformate of general formula V is used.

30. The process of claim 27, wherein the compounds of general formula I are prepared in the presence of a homogeneous or heterogeneous catalyst.

31. The process of claim 30, wherein the catalysts are heterogeneous.

32. The process of claim 30, wherein the catalysts are selected from the group consisting of $SnCl_4$, $SnCl_3Ph$, $AlCl_3$, $BBr_3$, $SbF_5$, $ZnCl_2$, $FeCl_3$, $BF_3$, $TiCl_4$, or any of the foregoing on an inert support, acidic montmorillonites, zeolites, or Envirocats®.

33. The process of claim 27 or 32, wherein the reaction mixture is neutralized to a defined degree using bases.

34. The process of claim 33, wherein the bases are selected from the group consisting of alcoholates or carbonates.

35. The process of claims 33, wherein any resulting solid salt-waste is mechanically removed.

36. The process of claim 35, wherein the mechanical removal of solid salt-waste is effected by a sparkler filter or a centrifuge.

37. The process of claim 27, wherein the compounds of general formula I are prepared in the presence of catalysts.

38. The process of claim 37, wherein the catalysts that are used for the elimination of the $R^5OH$ alcohols from the primarily formed compounds of general formula II are acidic in nature.

39. The process of claim 38, wherein the catalyst is a mildly acidic Lewis acid.

40. The process of claim 38, wherein the catalysts that are used for the elimination of the $R^5OH$ alcohols from the primarily formed compounds of general formula II are salts.

41. The process of claim 40, wherein the salts are transition metal salts.

42. The process of claim 41, wherein the transition metal salts are zinc salts and iron salts.

43. The process of claim 42, wherein the zinc salts are selected from the group consisting of $Zn(acac)_2$, $ZnSO_4$, $ZnCl_2$, $Zn(OAC)_2$, and the iron salt is $Fe(OAC)_2$.

44. The process of claim 38, wherein the catalysts that are used for the elimination of the $R^5OH$ alcohols from the primarily formed compounds of general formula II are heterogeneous catalysts.

45. The process of claim 44, wherein the heterogeneous catalysts are oxides.

46. The process of claim 45, wherein the oxides are metal oxides.

47. The process of claim 46, wherein the metal oxides are aluminum oxide or zinc oxide.

48. The process of claim 44, wherein the catalysts are selected from zeolites, silicas, montmorillonites, and metal-exchanged zeolites and montmorillonites.

49. The process of claim 27, wherein the primary reaction of the compounds of general formula IV and V is conducted at a lower temperature than the elimination of the alcohols of general formula $R^5OH$.

50. The process of claim 49, wherein the elimination of the alcohols of general formula $R^5OH$ is conducted in the temperature range from about 40° C. to 280° C.

51. The process of claim 50, wherein the temperature is from about 80° C. to about 230° C.

52. The process of claim 51, wherein the temperature range is from about 130° C. to about 190° C.

53. The process of claim 50, wherein the elimination of the alcohols of general formula $R^5OH$ is conducted during the distillation of the compounds of general formula I.

54. The process of claim 27, wherein the reaction is carried out in the presence of a trapping agent for the alcohols of general formula $R^5OH$.

55. The process of claim 54, wherein the trapping agent is an acid anhydride.

56. The process of claim 27, wherein any unconverted starting materials of general formula IV and V, as well as the products of general formula I, are recovered by distillation.

57. The process of claim 56, wherein the distillation is fractional distillation.

58. The process of claim 56 or 57, wherein exposure of the compounds of general formula V to the salt-wastes of the respective catalysts, which causes partial decomposition of the compounds of general formula V, is avoided.

59. The process of claims 27 or 57 wherein the presence of a catalyst favors the elimination of alcohols of the general formula $R^6OH$ from the compounds of general formula VI

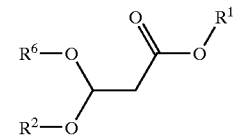

in which $R^6$ stands for $R^1$, $R^2$, $R^3$, $R^4$ or $R^5$, prior to, or during, the recovery of any unconverted compounds of general formula IV.

60. The process of claim 59, wherein the catalyst is a heterogeneous catalyst and or a waste resulting from neutralization of the primary reaction mixture.

61. The process of claim 27, wherein the reaction mixture is mixed with water followed by subsequent removal of the aqueous phase.

62. The process of claim 61, wherein the reaction mixture is mixed with an aqueous solution of a base followed by removal of the aqueous phase.

63. The process of claims 2 or 27, wherein the products of general formula I are further purified by distillation.

64. The process of claim 63, wherein fractional distillation is employed.

65. Methyl-3-methoxy-2-dimethoxymethyl-propenoate.

66. Ethyl-3-ethoxy-2-diethoxymethyl propenoate.

* * * * *